(12) United States Patent
Patel

(10) Patent No.: US 11,654,154 B2
(45) Date of Patent: May 23, 2023

(54) PROCESS FOR PREPARING INJECTABLE FOSAPREPITANT DIMEGLUMINE COMPOSITIONS HAVING IMPROVED STORAGE STABILITY

(71) Applicant: Navinta III Inc, Boca Raton, FL (US)

(72) Inventor: Sandipkumar Arvindbhai Patel, Robbinsville, NJ (US)

(73) Assignee: Navinta III Inc, Boca Raton, FL (US)

( * ) Notice: Subject to any disclaimer, the term of this patent is extended or adjusted under 35 U.S.C. 154(b) by 391 days.

(21) Appl. No.: 16/774,760

(22) Filed: Jan. 28, 2020

(65) Prior Publication Data

US 2020/0237788 A1 Jul. 30, 2020

Related U.S. Application Data

(60) Provisional application No. 62/798,223, filed on Jan. 29, 2019.

(51) Int. Cl.
*A61K 31/675* (2006.01)
*A61K 47/18* (2017.01)
*A61K 47/32* (2006.01)
*A61K 47/26* (2006.01)

(52) U.S. Cl.
CPC .......... *A61K 31/675* (2013.01); *A61K 47/183* (2013.01); *A61K 47/26* (2013.01); *A61K 47/32* (2013.01)

(58) Field of Classification Search
CPC .................................................. A61K 31/675
See application file for complete search history.

(56) References Cited

U.S. PATENT DOCUMENTS

| | | |
|---|---|---|
| 8,623,844 B2 | 1/2014 | Bhatt et al. |
| 9,913,853 B2 | 3/2018 | Malhotra et al. |
| 2015/0165045 A1 | 6/2015 | Karavas et al. |
| 2017/0119800 A1 | 5/2017 | Malhotra et al. |
| 2017/0348335 A1 | 12/2017 | Venturini et al. |
| 2018/0235973 A1 | 8/2018 | Chandrashekhar et al. |

FOREIGN PATENT DOCUMENTS

| | | | |
|---|---|---|---|
| CN | 102755296 A | * | 10/2012 |
| CN | 102755296 A | | 10/2012 |
| CN | 103565760 A | | 2/2014 |
| CN | 104971049 A | | 10/2015 |
| WO | 2018027029 A1 | | 2/2018 |
| WO | 2019038656 A1 | | 2/2019 |

OTHER PUBLICATIONS

Written Opinion for PCT/US 20/15570 (Opinion rendered Mar. 25, 2020). (Year: 2020).*
Horn, Jacqueline, et al. "Crystallizing amino acids as bulking agents in freeze-drying." European J. of Pharmaceutics and Biopharmaceutics. (2018), vol. 132, pp. 70-82. (Year: 2018).*
"Chemical Packaging: Disodium Edetate—Indications, Dosage, Side Effects and Precautions." (Last updated: Dec. 12, 2017). Accessed May 19, 2022. Available from: < https://www.medindia.net/doctors/drug_information/disodium_edetate.htm>. (Year: 2017).*
International Search Report Application No. PCT/US2020/015570; dated Apr. 28, 2020; 13 pages.
Akynzeo Prescribing Information, Revision dated Apr. 2018.
Emend Prescribing Information,Revision dated Mar. 2018.
Emend Prescribing Information, Revision dated Apr. 2018.
Hesketh et al., 2003, J Clin Oncol. 21:4112-4119.
EMA Assessment Report for Ivamend, European Medicines Agent Science Medicines Health, dated Jun. 24, 2010.
U.S. Pharmacopeia "USP", General Chapter <659>, "Packaging and Storage Requirements", revised May 26, 2017.
U.S. Pharmacopeia "USP", General Chapter <71>, "Sterility Tests", obtained from the internet on Jan. 28, 2020.

\* cited by examiner

*Primary Examiner* — John S Kenyon
(74) *Attorney, Agent, or Firm* — St. Onge Steward Johnston & Reens LLC

(57) ABSTRACT

Solid compositions having about 150 mg to about 245 mg Fosaprepitant that are stable after storage at about 25° C. for 6 months and processes for preparing solid Fosaprepitant compositions that are stable after long term storage at room temperature. The processes include freezing a Fosaprepitant solution in the primary packaging container at a first freezing temperature; applying vacuum at second temperature that is higher than the freezing temperature; fully stoppering the primary packaging container; and sealing the stoppered primary packaging container.

20 Claims, 15 Drawing Sheets

Figure 1: Summary of lyophilization trials 1 - 11

| Trial No. | Set pH of solution | Primary Drying Temperature | Secondary Drying Temperature | Vacuum | Initial Water content |
|---|---|---|---|---|---|
| 1 | 8.8 | -20°C | 25°C | 100 mT | 0.26% |
| 2 | 8.55 | -20°C | 25°C | 125 mT | 0.25% |
| 3 | 8.52 | -20°C | 25°C | 200 mT | 0.74% |
| 4 | 8.52 | -15°C | 25°C | 125 mT | 0.55% |
| 5 | 8.53 | -18°C | 25°C | 125 mT | 0.60% |
| 6 | 8.51 | -18°C | 25°C | 125 mT | 0.46% |
| 7 | 9.5 | -18°C | 25°C | 125 mT | 0.70% |
| 8 | 8.0 | -18°C | 25°C | 125 mT | 0.94% |
| 9 | 9.0 | -18°C | 25°C | 125 mT | 0.89% |
| 10 | 9.0 | -18°C | 25°C | 125 mT | 0.64% |
| 11 | 9.0 | -18°C | -5°C | 125 mT | 3.03% |

Figure 2: Finished Product and Stability Data of Trial No. 1

| Test | | Initial | 25°C/60%RH | | | | | | |
|---|---|---|---|---|---|---|---|---|---|
| | | | 1 Month | 2 Months | 3 Months | 6 Months | 12 Months | 24 Months |
| Description | | White lyophilized cake | White lyophilized cake | White lyophilized cake | White lyophilized cake | White lyophilized cake | White lyophilized cake | White lyophilized cake |
| Assay | | 101.0% | 99.2% | 100.1% | 98.5% | 96.2% | --- | 96.9% |
| pH | | 8.4 | 8.5 | 8.3 | 8.5 | 8.5 | 8.4 | 8.4 |
| Water content by KF | | 0.26% | 0.51% | 0.59% | 0.42% | 0.48% | 0.69% | 0.52% |
| Related Compounds | | | | | | | | |
| Aprepitant | | 0.71% | 0.89% | 0.77% | 0.78% | 0.96% | 1.59% | 1.8% |
| Any highest unspecified impurity | | 0.01% (RRT 0.66) | 0.01% (RRT 0.66) | 0.03% (RRT 0.65) | 0.03% (RRT 0.66) | 0.03% (RRT 0.65) | 0.03% (RRT 0.65) | 0.14% (RRT 4.09) |
| Total impurities | | 0.72% | 0.90% | 0.80% | 0.81% | 1.02% | 1.82% | 2.23% |
| Reconstitution time | | 17 seconds | 18 seconds | 17 seconds | 19 seconds | 20 seconds | 19 seconds | 7 seconds |
| Description of Reconstituted Solution | | clear colorless solution | clear colorless solution | clear colorless solution | clear colorless solution | clear colorless solution | clear colorless solution | clear colorless solution |
| Particulate matter in final diluted solution* (USP <788>) | ≥ 10μm | --- | --- | --- | --- | --- | --- | 3 Particles/mL |
| | ≥ 25μm | --- | --- | --- | --- | --- | --- | 0 Particles/mL |

*Lyophilized product was reconstituted using 5 mL 0.9% Sodium Chloride Injection and diluted up to 150 mL using 0.9% Sodium Chloride injection. According to USP <788> (Particulate matter in injections), the average number of particles present in the units tested does not exceed 25 per mL equal to or greater than 10 μm and does not exceed 3 per mL equal to or greater than 25 μm.

Figure 3: Finished Product and Stability Data of Trial No. 2

| Test | | Initial | 1 Month | 2 Months | 3 Months | 6 Months | 12 Months | 18 Months | 24 Months |
|---|---|---|---|---|---|---|---|---|---|
| | | | | | | 25°C/60%RH | | | |
| Description | | White lyophilized cake | White lyophilized cake | White lyophilized cake | White lyophilized cake | White lyophilized cake | White lyophilized cake | White lyophilized cake | White lyophilized cake |
| Assay | | 98.1% | 100.7% | 99.2% | 97.2% | 98.1% | 108.9% | 101.2% | 98.7% |
| pH | | 7.9 | 7.9 | 8.0 | 7.8 | 8.0 | --- | 7.9 | 7.9 |
| Water content by KF | | 0.25% | 0.56% | 0.39% | 0.36% | 0.39% | 0.50% | 0.49% | 0.55% |
| Related Compounds | | | | | | | | | |
| Aprepitant | | 0.83% | 0.77% | 0.97% | 0.92% | 1.06% | 1.35% | 1.6% | 1.9% |
| Any highest unspecified impurity | | 0.01% (RRT 0.66) | 0.03% (RRT 0.66) | 0.03% (RRT 0.66) | 0.03% (RRT 0.66) | 0.12% (RRT 4.14) | 0.09% (RRT 4.14) | 0.13% (RRT 4.17) | 0.14% (RRT 4.09) |
| Total Impurities | | 0.84% | 0.80% | 1.02% | 0.96% | 1.12% | 1.52% | 1.95% | 2.35% |
| Reconstitution time | | 18 seconds | 18 seconds | 19 seconds | 18 seconds | 22 seconds | --- | 17 seconds | 10 seconds |
| Description of Reconstituted Solution | | clear colorless solution | clear colorless solution | clear colorless solution | clear colorless solution | clear colorless solution | --- | clear colorless solution | clear colorless solution |
| Particulate matter in final diluted solution[1] (USP <788>) | ≥ 10μm | --- | --- | --- | --- | --- | --- | 3 Particles/mL | 4 Particles/mL |
| | ≥ 25μm | --- | --- | --- | --- | --- | --- | 0 Particles/mL | 1 Particles/mL |

[1] Lyophilized product was reconstituted using 5 mL 0.9% Sodium Chloride Injection and diluted up to 150 mL using 0.9% Sodium Chloride injection. According to USP <788> (Particulate matter in injections), the average number of particles present in the units tested does not exceed 25 per mL equal to or greater than 10 μm and does not exceed 3 per mL equal to or greater than 25 μm.

Figure 4: Finished Product and Stability Data of Trial No. 3

| Test | | Initial | 1 Month | 2 Months | 3 Months | 6 Months | 12 Months | 18 Months | 24 Months |
|---|---|---|---|---|---|---|---|---|---|
| | | | | | | 25°C/60%RH | | | |
| Description | | White lyophilized cake | White lyophilized cake | White lyophilized cake | White lyophilized cake | White lyophilized cake | White lyophilized cake | White lyophilized cake | White lyophilized cake |
| Assay | | 97.7% | 99.7% | 98.4% | 96.9% | 97.6% | 104.0% | 100.1% | 99.4% |
| pH | | 8.0 | 8.0 | 8.0 | 7.9 | 8.0 | --- | 7.9 | 8.0 |
| Water content by KF | | 0.74% | 0.76% | 0.65% | 0.56% | 0.76% | 0.61% | 0.80% | 0.85% |
| Related Compounds | | | | | | | | | |
| Aprepitant | | 0.85% | 0.73% | 0.96% | 0.87% | 0.96% | 1.23% | 1.5% | 1.8% |
| Any highest unspecified impurity | | 0.01% (RRT 0.66) | 0.03% (RRT 0.66) | 0.03% (RRT 0.66) | 0.03% (RRT 0.65) | 0.03% (RRT 0.65) | 0.09% (RRT 4.16) | 0.13% (RRT 4.17) | 0.15% (RRT 4.09) |
| Total impurities | | 0.86% | 0.76% | 1.01% | 0.92% | 1.02% | 1.38% | 1.85% | 2.23% |
| Reconstitution time | | 18 seconds | 17 seconds | 17 seconds | 17 seconds | 19 seconds | --- | 19 seconds | 9 seconds |
| Description of Reconstituted Solution | | clear colorless solution | clear colorless solution | clear colorless solution | clear colorless solution | clear colorless solution | --- | clear colorless solution | clear colorless solution |
| Particulate matter in final diluted solution[1] (USP <788>) | ≥10μm | --- | --- | --- | --- | --- | --- | 1 Particles/mL | 2 Particles/mL |
| | ≥25μm | --- | --- | --- | --- | --- | --- | 1 Particles/mL | 1 Particles/mL |

[1]Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 μm and does not exceed 3 per mL equal to or greater than 25 μm.

Figure 5: Finished Product and Stability Data of Trial No. 4

| Test | | Initial | 1 Month | 2 Months | 3 Months | 6 Months | 12 Months | 18 Months | 24 Months |
|---|---|---|---|---|---|---|---|---|---|
| | | | | | | 25°C/60%RH | | | |
| Description | | White lyophilized cake | White lyophilized cake | White lyophilized cake | White lyophilized cake | White lyophilized cake | White lyophilized cake | White lyophilized cake | White lyophilized cake |
| Assay | | 98.3% | 100.4% | 98.0% | 97.0% | 94.7% | 104.9% | 99.6% | 97.7% |
| pH | | 8.0 | 8.0 | 8.0 | 7.9 | 8.0 | --- | 7.9 | 7.9 |
| Water content by KF | | 0.55% | 0.51% | 0.49% | 0.44% | 0.53% | 0.62% | 0.70% | 0.70% |
| Related Compounds | | | | | | | | | |
| Aprepitant | | 0.86% | 0.74% | 0.85% | 0.93% | 1.01% | 1.28% | 1.5% | 1.8% |
| Any highest unspecified impurity | | 0.01% (RRT 0.66) | 0.03% (RRT 0.65) | 0.03% (RRT 0.66) | 0.03% (RRT 0.66) | 0.03% (RRT 0.65) | 0.08% (RRT 4.11) | 0.12% (RRT 4.18) | 0.16% (RRT 4.06) |
| Total impurities | | 0.87% | 0.77% | 1.00% | 0.97% | 1.04% | 1.59% | 1.83% | 2.24% |
| Reconstitution time | | 17 seconds | 17 seconds | 19 seconds | 18 seconds | 18 seconds | --- | 17 seconds | 8 seconds |
| Description of Reconstituted Solution | | clear colorless solution | clear colorless solution | clear colorless solution | clear colorless solution | clear colorless solution | --- | clear colorless solution | clear colorless solution |
| Particulate matter in final diluted solution* (USP <788>) | ≥10μm | --- | --- | --- | --- | --- | --- | 2 Particles/mL | 3 Particles/mL |
| | ≥25μm | --- | --- | --- | --- | --- | --- | 0 Particles/mL | 0 Particles/mL |

*Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 μm and does not exceed 3 per mL equal to or greater than 25 μm Figure 6: Finished Product and Stability Data of Trial No. 5

| Test | | Initial | 1 Month | 2 Months | 3 Months | 25°C/60%RH 6 Months | 12 Months | 18 Months | 24 Months |
|---|---|---|---|---|---|---|---|---|---|
| Description | | White lyophilized cake | White lyophilized cake | White lyophilized cake | White lyophilized cake | White lyophilized cake | White lyophilized cake | White lyophilized cake | White lyophilized cake |
| Assay | | 96.2% | 100.2% | 101.2% | 95.4% | 93.6% | 101.5% | 98.5% | 94.3% |
| pH | | 8.1 | 8.0 | 8.1 | 7.9 | 8.0 | --- | 8.0 | 8.0 |
| Water content by KF | | 0.60% | 0.58% | 0.44% | 0.44% | 0.47% | 0.57% | 0.44% | 0.58% |
| Related Compounds | | | | | | | | | |
| Aprepitant | | 0.86% | 0.77% | 0.82% | 0.90% | 1.02% | 0.86% | 1.5% | 1.8% |
| Any highest unspecified impurity | | 0.01% (RRT 0.66) | 0.03% (RRT 0.66) | 0.03% (RRT 0.66) | 0.03% (RRT 0.66) | 0.03% (RRT 0.65) | 0.07% (RRT 4.18) | 0.12% (RRT 4.18) | 0.16% (RRT 4.08) |
| Total Impurities | | 0.87% | 0.80% | 0.85% | 0.94% | 1.05% | 0.98% | 1.84% | 2.24% |
| Reconstitution time | | 16 seconds | 17 seconds | 18 seconds | 18 seconds | 21 seconds | --- | 15 seconds | 12 seconds |
| Description of Reconstituted Solution | | clear colorless solution | clear colorless solution | clear colorless solution | clear colorless solution | clear colorless solution | --- | clear colorless solution | clear colorless solution |
| Particulate matter in final diluted solution* (USP <788>) | ≥ 10μm | --- | --- | --- | --- | --- | --- | 6 Particles/mL | 2 Particles/mL |
| | ≥ 25μm | --- | --- | --- | --- | --- | --- | 1 Particles/mL | 0 Particles/mL |

*Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 μm and does not exceed 3 per mL equal to or greater than 25 μm.

Figure 7: Finished Product and Stability Data of Trial No. 6

| Test | Initial | 25°C/60%RH | | | | |
|---|---|---|---|---|---|---|
| | | 1 Month | 2 Months | 3 Months | 6 Months |
| Description | White lyophilized cake | White lyophilized cake | White lyophilized cake | White lyophilized cake | White lyophilized cake |
| Assay | 108.5% | 108.4% | 107.5% | 106.8% | 107.2% |
| pH | 8.0 | 8.0 | 8.0 | 7.9 | 8.0 |
| Water content by KF | 0.46% | 0.61% | 0.48% | 0.53% | 0.53% |
| Related Compounds | | | | | |
| Aprepitant | 0.91% | 0.83% | 0.99% | 0.87% | 1.2% |
| Any highest unspecified impurity | 0.02% (RRT 0.66) | 0.03% (RRT 0.66) | 0.03% (RRT 0.66) | 0.03% (RRT 0.66) | 0.10% (RRT 4.05) |
| Total Impurities | 0.93% | 0.86% | 1.03% | 0.94% | 1.4% |
| Reconstitution time | 16 seconds | 17 seconds | 18 seconds | 18 seconds | 18 seconds |
| Description of Reconstituted Solution | clear colorless solution | clear colorless solution | clear colorless solution | clear colorless solution | clear colorless solution |

Figure 8: Finished Product and Stability Data of Trial No. 7

| Test | Initial | 25°C/60%RH | | | | | |
|---|---|---|---|---|---|---|---|
| | | 1 Month | 2 Months | 3 Months | 6 Months | 12 Months | 24 Months |
| Description | White lyophilized cake | White lyophilized cake | White lyophilized cake | White lyophilized cake | White lyophilized cake | White lyophilized cake | White lyophilized cake |
| Assay | 97.6% | 100.6% | 100.2% | 97.1% | 96.4% | 102.4% | 94.0% |
| pH | 9.0 | 8.9 | 9.0 | 9.0 | 9.1 | --- | 9.1 |
| Water content by KF | 0.70% | 0.69% | 0.57% | 0.64% | 0.57% | 0.66% | 0.73% |
| Related Compounds | | | | | | | |
| Aprepitant | 0.37% | 0.60% | 0.69% | 0.76% | 0.95% | 1.16% | 1.5% |
| Any highest unspecified impurity | 0.02% (RRT 0.65) | 0.02% (RRT 0.66) | 0.02% (RRT 0.66) | 0.03% (RRT 0.66) | 0.09% (RRT 4.04) | 0.10% (RRT 4.18) | 0.13% (RRT 4.09) |
| Total Impurities | 0.40% | 0.62% | 0.72% | 0.81% | 1.2% | 1.35% | 2.0% |
| Reconstitution time | 16 seconds | 18 seconds | 17 seconds | 17 seconds | 19 seconds | --- | 10 seconds |
| Description of Reconstituted Solution | clear colorless solution | clear colorless solution | clear colorless solution | clear colorless solution | clear colorless solution | --- | Clear colorless solution |
| Particulate matter in final diluted solution* (USP <788>) ≥ 10μm | --- | --- | --- | --- | --- | --- | 2 Particles/mL |
| ≥ 25μm | --- | --- | --- | --- | --- | --- | 1 Particles/mL |

*Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 μm and does not exceed 3 per mL equal to or greater than 25 μm.

Figure 9: Finished Product and Stability Data of Trial No. 8

| Test | Initial | 1 Month | 2 Months | 3 Months | 6 Months | 12 Months | 24 Months |
|---|---|---|---|---|---|---|---|
| | | | | 25°C/60%RH | | | |
| Description | White lyophilized cake | White lyophilized cake | White lyophilized cake | White lyophilized cake | White lyophilized cake | White lyophilized cake | White lyophilized cake |
| Assay | 106.2% | 103.5% | 105.9% | 106.0% | 102.3% | 103.7% | 100.2% |
| pH | 7.8 | 7.7 | 7.9 | 7.8 | 7.7 | --- | 7.7 |
| Water content by KF | 0.94% | 0.61% | 0.60% | 0.65% | 0.67% | 0.74% | 0.68% |
| Related Compounds | | | | | | | |
| Aprepitant | 0.50% | 0.65% | 0.97% | 1.04% | 1.3% | 1.61% | 2.2% |
| Any highest unspecified impurity | 0.03% (RRT 0.65) | 0.03% (RRT 0.65) | 0.03% (RRT 0.66) | 0.03% (RRT 0.66) | 0.09% (RRT 4.04) | 0.11% (RRT 4.16) | 0.14% (RRT 4.08) |
| Total Impurities | 0.56% | 0.68% | 1.01% | 1.09% | 1.5% | 1.83% | 2.64% |
| Reconstitution time | 17 seconds | 18 seconds | 19 seconds | 19 seconds | 18 seconds | --- | 8 seconds |
| Description of Reconstituted Solution | clear colorless solution | clear colorless solution | clear colorless solution | clear colorless solution | clear colorless solution | --- | Clear colorless solution |
| Particulate matter in final diluted solution* (USP <788>) ≥ 10µm | --- | --- | --- | --- | --- | --- | 2 Particles/mL |
| ≥ 25µm | --- | --- | --- | --- | --- | --- | 1 Particles/mL |

*Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 µm and does not exceed 3 per mL equal to or greater than 25 µm.

Figure 10: Finished Product and Stability Data of Trial No. 9

| Test | | Initial | 25°C/60%RH | | | | | |
|---|---|---|---|---|---|---|---|---|
| | | | 1 Month | 2 Months | 3 Months | 6 Months | 12 Months | 24 Months |
| Description | | White lyophilized cake | White lyophilized cake | White lyophilized cake | White lyophilized cake | White lyophilized cake | White lyophilized cake | White lyophilized cake |
| Assay | | 107.6% | 103.9% | 106.6% | 105.4% | 104.0% | 103.6% | 102.6% |
| pH | | 8.6 | 8.5 | 8.6 | 8.6 | 8.6 | --- | 8.6 |
| Water content by KF | | 0.89% | 0.75% | 0.68% | 0.76% | 0.71% | 0.70% | 1.09% |
| Related Compounds | | | | | | | | |
| Aprepitant | | 0.46% | 0.66% | 0.83% | 0.87% | 1.1% | 1.37% | 1.8% |
| Any highest unspecified impurity | | 0.03% (RRT 0.65) | 0.03% (RRT 0.65) | 0.03% (RRT 0.66) | 0.03% (RRT 0.66) | 0.09% (RRT 4.05) | 0.11% (RRT 4.14) | 0.14% (RRT 4.08) |
| Total Impurities | | 0.52% | 0.69% | 0.87% | 0.92% | 1.3% | 1.62% | 2.21% |
| Reconstitution time | | 17 seconds | 17 seconds | 18 seconds | 18 seconds | 17 seconds | --- | 9 seconds |
| Description of Reconstituted Solution | | clear colorless solution | clear colorless solution | clear colorless solution | clear colorless solution | clear colorless solution | --- | Clear colorless solution |
| Particulate matter in final diluted solution* (USP <788>) | ≥ 10μm | --- | --- | --- | --- | --- | --- | 2 Particles/mL |
| | ≥ 25μm | --- | --- | --- | --- | --- | --- | 0 Particles/mL |

*Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 μm and does not exceed 3 per mL equal to or greater than 25 μm.

Figure 11: Finished Product and Stability Data of Trial No. 10

| Test | | Initial | 1 Month | 2 Months | 3 Months | 6 Months | 12 Months | 24 Months |
|---|---|---|---|---|---|---|---|---|
| | | | | | 25°C/60%RH | | | |
| Description | | White lyophilized cake | White lyophilized cake | White lyophilized cake | White lyophilized cake | White lyophilized cake | White lyophilized cake | White lyophilized cake |
| Assay | | 112.3% | 108.0% | 109.5% | 110.0% | 109.3% | 103.9% | 106.9% |
| pH | | 8.4 | 8.5 | 8.4 | 8.6 | 8.6 | --- | 8.5 |
| Water content by KF | | 0.64% | 0.66% | 0.81% | --- | 0.70% | 0.76% | --- |
| Related Compounds | | | | | | | | |
| Aprepitant | | 0.55% | 0.63% | 0.73% | 0.90% | 1.1% | 1.0% | 1.5% |
| Any highest unspecified impurity | | 0.03% (RRT 0.65) | 0.03% (RRT 0.66) | 0.03% (RRT 0.66) | 0.03% (RRT 0.66) | 0.10% (RRT 4.05) | 0.09% (RRT 4.16) | 0.15% (RRT 4.08) |
| Total impurities | | 0.58% | 0.68% | 0.81% | 0.96% | 1.3% | 1.14% | 1.95% |
| Reconstitution time | | 18 seconds | 17 seconds | 19 seconds | --- | 19 seconds | --- | 12 seconds |
| Description of Reconstituted Solution | | clear colorless solution | clear colorless solution | clear colorless solution | --- | Clear colorless solution | --- | Clear colorless solution |
| Particulate matter in final diluted solution* (USP <788>) | ≥ 10μm | --- | --- | --- | --- | --- | --- | 2 Particles/mL |
| | ≥ 25μm | --- | --- | --- | --- | --- | --- | 0 Particles/mL |

*Lyophilized product was reconstituted using 5 mL 0.9% Sodium Chloride Injection and diluted up to 150 mL using 0.9% Sodium Chloride Injection. According to USP <788> (Particulate matter in injections), the average number of particles present in the units tested does not exceed 25 per mL equal to or greater than 10 μm and does not exceed 3 per mL equal to or greater than 25 μm.

Figure 12: Finished Product and Stability Data of Trial No. 11

| Test | Initial | 25°C/60%RH | | | |
|---|---|---|---|---|---|
| | | 1 Month | 2 Months | 3 Months | 6 Months |
| Description | White lyophilized cake | White lyophilized cake | White lyophilized cake | White lyophilized cake | White lyophilized cake |
| Assay | 111.4% | 112.9% | 108.7% | 112.1% | 108.9% |
| pH | 8.4 | 8.5 | 8.4 | 8.6 | 8.5 |
| Water content by KF | 3.03% | 3.15% | 3.18% | --- | 3.05% |
| Related Compounds | | | | | |
| Aprepitant | 0.54% | 0.57% | 0.68% | 0.90% | 1.1% |
| Any highest unspecified impurity | 0.03% (RRT 0.65) | 0.03% (RRT 0.66) | 0.03% (RRT 0.66) | 0.03% (RRT 0.66) | 0.10% (RRT 4.05) |
| Total Impurities | 0.57% | 0.62% | 0.76% | 0.96% | 1.3% |
| Reconstitution time | 18 seconds | 19 seconds | 19 seconds | --- | 18 seconds |
| Description of Reconstituted Solution | clear colorless solution | clear colorless solution | clear colorless solution | --- | Clear colorless solution |

Figure 13: Reconstituted solution stability study performed after 26 months storage at 25°C (room temperature)

| Test | | Trial No. 1 | | Trial No. 8 | | Trial No. 9 | |
|---|---|---|---|---|---|---|---|
| | | 0 Hr | 24 Hrs. | 0 Hr | 24 Hrs. | 0 Hr | 24 Hrs. |
| Reconstitution time | | <30 seconds | --- | <30 seconds | --- | <30 seconds | --- |
| Description of Reconstituted solution | | Clear colorless solution | --- | Clear colorless solution | --- | Clear colorless solution | --- |
| Description of final diluted solution | | Clear colorless solution | Clear colorless solution | Clear colorless solution | Clear colorless solution | Clear colorless solution | Clear colorless solution |
| Assay by HPLC | | 103.6% | 101.1% | 102.8% | 99.7% | 104.2% | 101.7% |
| Related Substances by HPLC | Aprepitant Any unspecified impurity | 1.5% | 1.7% | 1.9% | 2.0% | 1.6% | 1.6% |
| | Total Impurities (Excluding Aprepitant) | 0.14% | 0.14% | 0.13% | 0.13% | 0.13% | 0.13% |
| | | 0.4% | 0.4% | 0.4% | 0.4% | 0.4% | 0.4% |
| Particulate matter in final diluted solution (USP <788>)* | ≥ 10μm | 10 Particles | 20 Particles | 19 Particles | 9 Particles | 11 Particles | 19 Particles |
| | ≥ 25μm | 1 Particle | 1 Particle | 1 Particle | 1 Particle | 1 Particle | 1 Particle |

*According to USP <788> particulate matter for large volume parenteral (>100 mL) should be not more than 25 particles of size ≥ 10μm and not more than 3 particles of size ≥ 25μm Figure 14: Reconstituted solution stability study (in-use) performed after exposing sample at 50°C for 21 days for higher aprepitant

| Test | | Trial No. 8 exposed to 50°C for 21 days before in-use study | |
|---|---|---|---|
| | | 0 Hr | 24 Hrs. |
| Reconstitution time | | <30 sec | --- |
| Description of Reconstituted solution | | Clear colourless solution | --- |
| Description of final diluted solution | | Clear colourless solution | Colourless solution with very fine crystals |
| Assay by HPLC | | 108.6% | 106.6% |
| Related Substances by HPLC | Aprepitant: Any unspecified impurity: | 3.7% 0.16% | 3.7% 0.16% |
| | Total Impurities (Excluding Aprepitant): | 0.4% | 0.4% |
| Particulate matter in final diluted solution (USP <788>)* | ≥ 10µm | 18 particles | 36 particles |
| | ≥ 25µm | 0 particles | 0 particles |

*According to USP <788> particulate matter for large volume parenteral (>100 mL) should be not more than 25 particles of size ≥ 10µm and not more than 3 particles of size ≥ 25µm]

Figure 15: Analytical results of EMEND® (Fosaprepitant) for Injection, 150 mg/vial

| Product Name: EMEND® (Fosaprepitant) for Injection, 150 mg/vial | | | | |
|---|---|---|---|---|
| Manufactured by: Merck & Co. | Storage Condition: Stored at 2° to 8°C (36° to 46°F). | | | |
| Lot No. | R005352 | N028282 | N031936 | |
| Exp. Date: | Nov. 04, 2019 | June 18, 2019 | Feb. 19, 2019 | |
| Analysis Completion Date: | Jul. 03, 2018 | Nov. 20, 2019 | Jul. 03, 2018 | Jul. 01, 2019 | Jul. 03, 2018 | Feb. 25, 2019 |
| Test | Result | | | | | |
| Assay | 106.8% | --- | 104.1% | --- | 100.8% | --- |
| pH | 8.43 | --- | 8.43 | --- | 8.42 | --- |
| Reconstitution time | 50 Seconds | --- | 49 Seconds | --- | 52 Seconds | --- |
| Completeness and clarity of solution | Complies | --- | Complies | --- | Complies | --- |
| Related Substances | | | | | | |
| Aprepitant | 0.16% | 0.20% | 0.16% | 0.20% | 0.15% | 0.19% |
| Any highest unspecified impurity | 0.16% | 0.14% | 0.11% | 0.13% | 0.09% | 0.09% |
| Total impurities (excluding Aprepitant) | 0.22% | 0.20% | 0.19% | 0.22% | 0.21% | 0.20% |

PROCESS FOR PREPARING INJECTABLE FOSAPREPITANT DIMEGLUMINE COMPOSITIONS HAVING IMPROVED STORAGE STABILITY

FIELD OF THE INVENTION

The present invention relates to processes for preparing injectable pharmaceutical compositions comprising Fosaprepitant or a suitable salt thereof that can be stored at ambient temperature (about 20-25° C.) and compositions made according to such processes.

BACKGROUND OF THE INVENTION

Nausea and vomiting, which often follow chemotherapy, are severe and distressing side effects of many chemotherapeutics. Current treatment of these effects includes nurokinin-1 (NK1) receptor antagonists and 5-hydroxytryptamine 3 (5-HT3) receptor antagonists to a subject in need thereof. With the intent of developing more effective treatments for chemotherapy induced nausea and vomiting (CINV), studies were carried out to demonstrate the efficacy of combining the NK-1 receptor antagonist Aprepitant with a 5-HT3 receptor antagonist (ondansetron) and a corticosteroid (dexamethasone). Results showed that addition of Aprepitant to a standard treatment regimen of ondansetron and dexamethasone was generally well-tolerated and provided consistently superior protection against CINV in subjects receiving highly emetogenic cisplatin-based chemotherapy (Hesketh et al., 2003, J Clin Oncol. 21:4112-4119).

Fosaprepitant has good solubility in water, while its degradant Aprepitant has minimal solubility. Therefore, for certain formulations, it is desirable to use Fosaprepitant as the active agent. However, a major stability issue with Fosaprepitant is its hydrolysis in aqueous media to form the parent Aprepitant, which is practically insoluble in water and generates particles in an injectable solution, which is undesirable. To avoid degradation of Fosaprepitant to Aprepitant in aqueous media, Fosaprepitant is lyophilized to remove water. Scientific discussion in the EMA application for lyophilized Fosaprepitant product describes that "The process has been optimized to prevent degradation of Fosaprepitant during manufacture especially with regard to temperature, pH, and water content."

U.S. Pat. No. 9,913,853 teaches a liquid composition comprising Fosaprepitant or a salt thereof and at least one liquid excipient, wherein after storage at 2-8° C. for at least 1 month, aprepitant is present in an amount concentration of no more than 10%, wherein the composition is ready-to-use or ready-to-dilute.

AKYNZEO® is a combination drug product of Fosnetupitant recently approved by United States Food and Drug Administration. AKYNZEO® (235 mg fosnetupitant/0.25 mg palonosetron) for injection is a combination product of fosnetupitant, a prodrug of netupitant, which is a substance P/neurokinin 1 (NK-1) receptor antagonist, and palonosetron hydrochloride, a serotonin-3 (5-HT3) receptor antagonist. AKYNZEO® for injection is available for intravenous infusion and is supplied as a sterile lyophilized powder in a single-dose vial. Each vial contains 235 mg of fosnetupitant (equivalent to 260 mg fosnetupitant chloride hydrochloride) and 0.25 mg of palonosetron (equivalent to 0.28 mg of palonosetron hydrochloride). The inactive ingredients are edetate disodium (6.4 mg), mannitol (760 mg), sodium hydroxide and/or hydrochloric acid (for pH adjustment). The storage of this approved product is 2-8° C.

EMEND (Fosaprepitant Dimeglumine) for Injection, 150 mg/vial manufactured by Merck & Co is also supplied as a lyophilized product. The indication of EMEND is prevention of nausea and vomiting associated with highly emetogenic cancer chemotherapy and moderately emetogenic cancer chemotherapy. The labeling for Emend states that "EMEND for injection vials must be refrigerated, store at 2° C.-8° C. (36° F.-46° F.)". The lyophilized product is used by reconstituting and further diluting the reconstituted lyophile before administration to patient. The product should be reconstituted using 5 mL 0.9% Sodium chloride Injection and further diluted to 150 mL using 0.9% Sodium Chloride Injection. The storage of the final diluted solution is at or below 25° C. (or room temperature) up to 24 hours.

The composition of EMEND pre-lyophilization solution and the lyophilization parameters are not publicly available. However, based on the generally available information, lyophilized products of Fosaprepitant or a salt thereof can only be stored at 2-8° C. To remain stable, the finished products of Fosaprepitant (lyophilized or liquid dosage form) need to be stored at 2-8° C., which requires refrigeration for transportation and long-term storage. However, storage and transportation of pharmaceutical products at refrigerated conditions is more costly and cumbersome.

Any pharmaceutical product stored at refrigerated condition requires cold chain for transportation and a refrigeration system for long term storage. In contrast, controlled room temperature storage condition is most convenient and easier to control in day to day practice. Therefore, the most preferred storage condition for pharmaceutical products is controlled room temperature (about 20° C.-25° C.).

There is a desire for Fosaprepitant compositions that can be stored at room temperature without any need to refrigerate the compositions for long term storage.

There is a desire for solid Fosaprepitant compositions that can be stored at room temperature without any need to refrigerate the compositions for long term storage.

There is desire for solid Aprepitant containing Fosaprepitant compositions that can be stored at room temperature without any need to refrigerate the compositions for long term storage.

As Aprepitant is the compound that has therapeutic activity, there is a desire for solid Fosaprepitant compositions that contain Aprepitant but in amounts that are soluble and will not create particulates when prepared for parenteral administration. There is a desire to have solid formulations of Fosaprepitant in which the amount of Aprepitant is greater than 0.5% but less than 10% by weight upon storage at ICH conditions, and most desirably room temperature storage.

There is a desire to have improved processes for preparing Fosaprepitant compositions, such that they produce products that are stable when stored and transported at controlled room temperature and are able to control the amount of Aprepitant.

SUMMARY OF THE INVENTION

The inventor has surprisingly found processes that produce pharmaceutical compositions of Fosaprepitant or its salts that can be stored at room temperature for long term storage and which can control the amount of Aprepitant.

A process for preparing solid Fosaprepitant compositions that are stable after long term storage at room temperature comprises the steps of dissolving Fosaprepitant active ingredient and any excipients in water to form a Fosaprepitant solution; filtering the Fosaprepitant solution; filling the filtered solution into a primary packaging container; partially stoppering the primary packaging container; freezing the solution in the primary packaging container at a first freezing temperature; applying vacuum at second temperature that is higher than the freezing temperature; fully stoppering the primary packaging container; and sealing the stoppered primary packaging container.

In some embodiments, the step of dissolving comprises dissolving the Fosaprepitant active ingredient and excipients in a first quantity of water and then subsequently adding a second quantity of water.

In certain embodiments, the primary packaging container is a vial and the step of partially stoppering comprises half stoppering the vial.

In certain embodiments, the Fosaprepitant solution is held for at least 72 hours before and/or after the step of filtering and prior to the step of filling.

In some embodiments, the freezing temperature is about −35° C. to about −55° C., preferably about −35° C. to −45° C.

In certain embodiments, the second temperature is about −25° C. to about −5° C., preferably about −5° C. to about −20° C.

In some embodiments, the vacuum is about 500 mT to about 100 mT, preferably about 100 mT to about 200 mT.

In certain embodiments, after the step of the applying vacuum, the process further comprises the step of secondary drying at a temperature greater than 0° C.

In some preferred embodiments, the excipients comprise a surface active agent. In some of those embodiments, the surface active agent comprises Polysorbate 80. In certain embodiments, the concentration of surface active agent in the Fosaprepitant solution is 10 mg/mL to 30 mg/mL.

In certain embodiments, the excipients comprise at least one of a chelating agent and a bulking agent.

In some embodiments, the process further comprises the step of adjusting the pH of the Fosaprepitant solution to be between pH 7 and 9.5.

In certain preferred embodiments, the Fosaprepitant active ingredient is Fosaprepitant Dimeglumine.

In some embodiments, the Fosaprepitant solution has a concentration of about 5 mg/mL to about 150 mg/mL.

The invention also comprises a solid Fosaprepitant composition produced by the inventive processes.

In some embodiments, the composition comprises about 150 mg to about 245 mg Fosaprepitant or pharmaceutically acceptable salt thereof, and after storage at about 25° C. for about 6, 7, 8, 9, 10, 11 and/or 12 months, a solution obtained after reconstitution of the solid composition with 0.9% Sodium Chloride Injection followed by dilution up to 150/ mg mL using 0.9% Sodium Chloride Injection has an average number of particles that does not exceed 25 per mL equal to or greater than 10 μm and 3 per mL equal to or greater than 25 μm.

In certain embodiments, after storage for 24 hours at room temperature of the solution obtained after reconstitution and dilution the average number of particles present does not exceed 25 per mL equal to or greater than 10 μm and does not exceed 3 per mL equal to or greater than 25 μm.

The invention further comprises a solid composition comprising about 150 mg of Fosaprepitant, wherein after storage at about 25° C. for about 6, 7, 8, 9, 10, 11, and/or 12 months, preferably 12 months, the product contains less than 2.5% of Aprepitant.

In certain preferred embodiments, the composition contains at least one of Polysorbate 80, lactose, and Disodium Edetate.

In some embodiments, the composition contains pH adjusting agent. In some embodiments, the composition contains povidone.

In certain embodiments, Aprepitant is not present in the compositions at more than 5.0%, preferably 3.5%, more preferably 2.0%, after 6, 7, 8, 9, 10, 11, and/or 12 months, preferably 12, months storage at room temperature. In some embodiments, Aprepitant is not present in the compositions at more than 2.5%, preferably 2.0%, after 24 months storage at room temperature.

In certain preferred embodiments, the total impurities are not more than 7.0%, more preferably 2.0%, after 6, 7, 8, 9, 10, 11, and/or 12 months, preferably 12, months storage at room temperature. In some embodiments, the total impurities are not more than 3.0% after 24 months storage at room temperature.

Alternatively, the invention comprises solid compositions comprising about 150 mg to about 245 mg of Fosaprepitant, wherein after storage at about 25° C. for 6, 7, 8, 9, 10, 11 and/or 12 months, preferably 12 months, the solid compositions contain greater than 0.5% but less than 10% by weight Aprepitant, more preferably about 1% to about 3.5% by weight Aprepitant.

In yet another embodiment, the invention provides a room temperature stable solid pharmaceutical composition comprising about 150 mg to about 245 mg Fosaprepitant or pharmaceutically acceptable salt thereof and 0.5% to 3.5% by weight Aprepitant.

DESCRIPTION OF THE DRAWINGS

FIG. 1 is a summary of 11 lyophilization trials for preparation of compositions of the invention.

FIG. 2 shows stability testing data after storage at 25° C./60% RH of product lyophilized according to trial 1 of FIG. 1.

FIG. 3 shows stability testing data after storage at 25° C./60% RH of product lyophilized according to trial 2 of FIG. 1.

FIG. 4 shows stability testing data after storage at 25° C./60% RH of product lyophilized according to trial 3 of FIG. 1.

FIG. 5 shows stability testing data after storage at 25° C./60% RH of product lyophilized according to trial 4 of FIG. 1.

FIG. 6 shows stability testing data after storage at 25° C./60% RH of product lyophilized according to trial 5 of FIG. 1.

FIG. 7 shows stability testing data after storage at 25° C./60% RH of product lyophilized according to trial 6 of FIG. 1.

FIG. 8 shows stability testing data after storage at 25° C./60% RH of product lyophilized according to trial 7 of FIG. 1.

FIG. 9 shows stability testing data after storage at 25° C./60% RH of product lyophilized according to trial 8 of FIG. 1.

FIG. 10 shows stability testing data after storage at 25° C./60% RH of product lyophilized according to trial 9 of FIG. 1.

FIG. 11 shows stability testing data after storage at 25° C./60% RH of product lyophilized according to trial 10 of FIG. 1.

FIG. 12 shows stability testing data after storage at 25° C./60% RH of product lyophilized according to trial 11 of FIG. 1.

FIG. 13 shows results of reconstituted solution stability testing of product lyophilized according to trial 1, 8, and 9 of FIG. 1 after 26 months storage at room temperature.

FIG. 14 shows results of reconstituted solution stability testing of product lyophilized according to trial 8 of FIG. 1 after exposure to 50° C. for 21 days.

FIG. 15 shows results of testing various lots of commercial EMEND 150 mg/vial product for assay, pH, reconstitution time, solution clarity and degradants and impurities.

DETAILED DESCRIPTION OF THE INVENTION

The inventor has surprisingly found processes that produce lyophilized Fosaprepitant Dimeglumine for Injection, 150 mg/vial that can be stored at controlled room temperature (20-25° C.) for more than 6 months, and preferably 24 months. The Aprepitant (the degradant of Fosaprepitant) is present less than about 3.0% after about 12-24 months and total impurities are less than about 5.0%. Such products present substitutable alternatives to EMEND but that are easier to store and distribute. In turn, the compositions provide low cost generic alternatives to EMEND. They are advantageous in that they are lower cost due not only to being generic therapeutic equivalents but also because they are easier to store and distribute. Thus, there are costs savings to all parties involved in the supply chain as well as the customer.

The United States Pharmacopoeia defines controlled room temperature as the temperature maintained thermostatically that encompasses the usual and customary working environment of 20°-25° (68°-77° F.). The following conditions also apply: Mean kinetic temperature not to exceed 25°. Thus, excursions between 15° and 30° (59° and 86° F.) that are experienced in pharmacies, hospitals, and warehouses, and during shipping are allowed, provided the mean kinetic temperature does not exceed 25° C., and transient spikes up to 40° are permitted as long as they do not exceed 24 hours. As used herein, the term "controlled room temperature" has the same meaning as given in 41 USP.

A process for preparing Fosaprepitant compositions that are stable at controlled room temperature comprises the steps of preparing a pre-lyophilization solution, the solution comprising Fosaprepitant active ingredient and water, and lyophilizing the pre-lyophilization solution. The pre-lyophilization solution is prepared prior to lyophilization to make dried cake or powder. The freeze-dried product is reconstituted prior to dilution for administration to a patient.

The pre-lyophilization solutions comprise Fosaprepitant active ingredient, i.e. Fosaprepitant or a pharmaceutically acceptable salt thereof dissolved in water. The preferred concentration Fosaprepitant in the pre-lyophilization solution is 37.5 mg/mL; however, the process is sufficient for preparing concentrations of about 5 mg/mL to about 150 mg/mL.

As used herein, the term "about" is defined as ±10%, preferably ±5%.

The term "pharmaceutically acceptable" as used herein means that which is useful in preparing a pharmaceutical composition that is generally safe and non-toxic.

The Fosaprepitant active ingredient is most preferably Fosaprepitant Dimeglumine. The concentration of the Fosaprepitant Dimeglumine in the resulting lyophilized composition may vary from about 5 wt % to 80 wt %, 10 wt % to 60 wt %, 20 wt % to 45 wt %, 30 wt % to 40 wt %. Most preferably, the amount of Fosaprepitant is one that corresponds to 150 mg in the primary packaging container, e.g. vial.

Preferably, the water is water for injection.

In certain embodiments, the pre-lyophilization solution includes bulking agent. A bulking agent may be present in formulation at about 5% to 60% w/w of the solid cake, preferably about 30% to 50% w/w. The bulking agent may be selected from the group consisting of, but not limited to, Lactose, Mannitol, Dextrose, Sucrose, Trehalose, Raffinose, Glycine, Sorbitol, Sodium Chloride, Potassium Chloride, Povidone, and Polyethylene glycol.

Any other inactive ingredient that can be used for parenteral administration and used for lyophilization as bulking agent or filler to form suitable lyophilized cake is also envisioned. In certain preferred embodiments, the bulking agent comprises Lactose.

The solutions preferably further comprise a surface active agent.

In certain preferable embodiments, the solutions comprise Polysorbate 80.

The surface-active agent may be present at about 5% to 30% w/w of the lyophilized composition, preferably about 10% to 25% w/w. In some embodiments, the surface active agent is present from about 10% to about 20% w/w. In other embodiments, the surface-active agent is present from about 10% to about 15% w/w, preferably 10% to 12% w/w. The concentration of surfactant is dependent on the amount of Fosaprepitant active ingredient, with higher concentrations of active requiring greater amounts of surfactant.

The solutions of the present invention may further comprise a tonicity adjusting agent. Tonicity adjusting agents suitable for use in pharmaceutical compositions described herein include, but are not limited to, anhydrous or hydrous forms of sodium chloride, dextrose, sucrose, xylitol, fructose, glycerol, sorbitol, mannitol, potassium chloride, mannose other inorganic salts except containing divalent cations. In certain preferable embodiments, the formulations comprise sodium chloride.

The solutions may optionally comprise chelating agent at about 0.5% to 5.0% w/w of the resulting solid composition, preferably about 0.5% to 2.0% w/w. Suitable chelating agents which may be used in the present invention include, but not limited to edetate disodium (EDTA); edetate trisodium; edetate tetrasodium; and diethyleneamine pentaacetate or derivatives thereof. In certain preferable embodiments, the formulations comprise disodium edetate.

In certain embodiments, the method comprises dissolving bulking agent, surface active agent, and chelating agent in water and then dissolving a required quantity of Fosaprepitant Dimeglumine in the solution.

In some embodiments, the method comprises adjusting pH of the Fosaprepitant solution to about 7 to 9.5 using pH adjusting agent or buffering agent.

Optionally, the solutions comprise pH adjusting agent or buffering agent at about 0% to 5% w/w of the solid composition, preferably about 0.05% to 2.0%.

Buffers suitable for use in the pharmaceutical compositions described herein include, but are not limited to, pharmaceutically acceptable salts and acids of acetate, glutamate, citrate, tartrate, benzoate, lactate, histidine or other amino acids, gluconate, phosphate, malate, succinate, formate, propionate, and carbonate.

Suitable pH adjusting agents which may be used in the present invention include, but not limited to sodium hydroxide, hydrochloric acid, citric acid, acetic acid, fumaric acid, hydrochloric acid, malic acid, nitric acid, phosphoric acid, propionic acid, sulfuric acid, tartaric acid, or combinations thereof. In certain preferable embodiments, the formulations comprise a pH adjusting agent. In some of those embodiments, the pH adjusting agent is sodium hydroxide and/or hydrochloric acid.

The method may further comprise filtering the Fosaprepitant solution through a sterilizing filter. In certain embodiments, the sterilizing filter is a 0.22µ or 0.45µ filter.

In some embodiments, the method further comprises filling the filtered solution in a container. In certain embodiments, the container is a glass vial. In some embodiments, the method comprises placing a stopper in the vial and partially stoppering it. Partial stoppering of vials provides space for removal of water as the vapor forms. Partially stoppered vials are easy to stopper fully after completion of lyophilization process.

The Fosaprepitant solutions are lyophilized. The term "lyophilized" and "lyophilization" (also known as freeze-drying, lyophilisation, or cryodesiccation) means a process of removal water or other solvents by freezing a material containing water and/or other solvents followed by reducing the surrounding pressure to allow the frozen water and/or other solvents in the material to sublimate directly from the solid phase to the gas phase. Lyophilization will result in a solid cake containing Fosaprepitant.

Preferably, the lyophilization cycle includes a freezing temperature, primary drying temperature, secondary drying temperature and vacuum.

In certain embodiments, the freezing temperature is −5° C. to −55° C., preferably −20° C. to −50° C., most preferably −45° C.

In certain embodiments, the primary drying temperature is −5° C. to −55° C., preferably −10° C. to −40° C., more preferably about −15° C. to −30° C., most preferably about −15° C. to −25° C.

In certain embodiments, the secondary drying temperature is about −10° C. to 25° C., preferably about −5° C. to 25° C., most preferably about 25° C.

In certain embodiments, the vacuum pressure (applied during primary drying and secondary drying) is about 500 mT, preferably about 200 mT, most preferably about 125 mT.

In some embodiments, after lyophilization, the container is sealed. As used herein, the term "seal" refers to any device or substance used to join two surfaces of a container or packaging so as to prevent them from coming apart or to prevent the contents from escaping. The step of "sealing" a container or packaging with a seal can occur simultaneous with, or after a Fosaprepitant solution is placed in the container or packaging. Means of sealing and packaging pharmaceutical solutions and solids in primary and secondary packaging are well known in the drug packaging arts and are meant to be included herein.

As used herein, the term "primary packaging" refers to materials that are in direct contact with the Fosaprepitant active ingredient. The primary packaging components (e.g. bottles, vials, closures) are in direct physical contact with the product whereas the secondary components are not.

Guidelines on suitable packaging for pharmaceutical products are published by e.g. the World Health Organization and are well known to those of skill in the art.

The resulting freeze dried formulations may be provided as a single unit lyophilized sterile pharmaceutical formulation of Fosaprepitant Dimeglumine for parenteral administration. In certain preferred embodiments, a single unit sterile pharmaceutical formulation is comprised of Fosaprepitant Dimeglumine and other excipients for parenteral administration.

In certain embodiments, the compositions of the present invention can be formulated as a "single use dosage," which refers to a premixed composition that is disposed within a sealed container or vessel as a one dose per container or vessel formulation.

The parenteral formulation produced by the inventive process can be injected intravenously. As a result, in particular preferred embodiments, the process produces formulations that are sterile.

As used here in the term "sterile" means a product that can be labeled as sterile and which provides a therapeutically acceptable Fosaprepitant composition. In some embodiments, sterile product meets the criteria of sterility according to the United States Pharmacopoeia 41 <71>, "41 USP". Further regulations for sterility of the final product include the European Pharmacopoeia (Ph. Eur. section 2.6.1), and the Japanese Pharmacopoeia (JP section 54). These methods have been harmonized with the USP methods and results generated under these sources can be considered equivalent to testing conducted according to USP <71>. Preferably, the therapeutically acceptable Fosaprepitant compositions have been produced by a method which provides assurance of sterility according to the US Pharmacopoeia US Pharmacopoeia 40 <71> or USP 41 <71>.

As used herein to describe the formulations of the present invention, the term "stable" means a change of not more than about 15% in the concentration of the active agents when measured by HPLC.

The pre-lyophilization solution is prepared prior to lyophilization to make dried cake or powder. The freeze-dried product is reconstituted prior to dilution for administration to a patient.

In some embodiments, the diluent for reconstitution is water for injection, 0.9% sodium chloride injection, 5% Dextrose, or any other suitable pharmaceutical fluid or combination thereof for parenteral administration.

In some embodiments, the process results in a Fosaprepitant formulation product that is a sterile liquid injectable. For administration to a patient in need thereof, the solution may be further diluted at least 5 times before parenteral administration.

In accordance with the present disclosure, Fosaprepitant may be administered to a patient in a quantity sufficient to treat or prevent the symptoms, and/or underlying etiology associated with emesis in the patient.

The present disclosure will now be described in connection with certain embodiments, which are not intended to be limiting in scope. On the contrary, the present application covers all alternatives, modifications, and equivalents as included within the scope of the claims. Thus, the following will illustrate the practice of the present disclosure, for the purposes of illustration of certain embodiments and is presented to provide what is believed to be a useful and readily understood description of its procedures and conceptual aspects.

EXAMPLES

Example 1

Preparation of Fosaprepitant Dimeglumine for Injection Lyophilized Product

Composition

| Ingredient | Qty/mL | Qty/vial | % w/w |
|---|---|---|---|
| Fosaprepitant Dimeglumine | 61.325 mg | 245.3 mg | 35.01 |
| Disodium Edetate | 1.35 mg | 5.4 mg | 0.77 |
| Polysorbate 80 | 18.75 mg | 75.0 mg | 10.70 |
| Lactose | 93.75 mg | 375.0 mg | 53.52 |
| Sodium Hydroxide | q.s. to pH | q.s. to pH | q.s. |
| Hydrochloric acid | q.s. to pH | q.s. to pH | q.s. |
| Water for Injection | q.s. to 1 mL | q.s. to 4 mL* | — |

*Water for Injection will be removed during lyophilization

Method Of Preparation of Solution for Lyophilization i. Take approx. 70% of batch required water for injection;
ii. Add and dissolve required quantity of Lactose;
iii. Add and dissolve required quantity of Disodium Edetate;
iv. Add and dissolve required quantity of Polysorbate 80;
v. Optionally, cool the solution to 2-8° C.
vi. Add and dissolve required quantity of Fosaprepitant Dimeglumine;
vii. Adjust pH to about 7 to 9.5 using sodium hydroxide and/or hydrochloric acid;
viii. Make the volume to batch size and filter using 0.22µ filter, fill 4 mL of filtered solution in glass vial and half stopper it; and
ix. Lyophilize it using below lyophilization cycle.

Lyophilization Cycles

| | | Trial 1 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 100 mT |
| | −20° C. | 250 | 3200 | 100 mT |
| | −5° C. | 250 | 120 | 100 mT |
| Secondary Drying | 25° C. | 375 | 600 | 100 mT |

| | | Trial 2 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 125 mT |
| | −20° C. | 250 | 3200 | 125 mT |
| | −5° C. | 250 | 120 | 125 mT |
| Secondary Drying | 25° C. | 375 | 600 | 125 |

| | | Trial 3 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 200 mT |
| | −20° C. | 250 | 3200 | 200 mT |
| | −5° C. | 250 | 120 | 200 mT |
| Secondary Drying | 25° C. | 375 | 600 | 200 mT |

| | | Trial 4 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 125 mT |
| | −15° C. | 150 | 2200 | 125 mT |
| | −5° C. | 250 | 120 | 125 mT |
| Secondary Drying | 25° C. | 375 | 600 | 125 mT |

| | | Trial 5 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 125 mT |
| | −18° C. | 270 | 3200 | 125 mT |
| | −5° C. | 250 | 120 | 125 mT |
| Secondary Drying | 25° C. | 375 | 600 | 125 mT |

| | | Trial 6 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 125 mT |
| | −18° C. | 270 | 3200 | 125 mT |
| | −5° C. | 250 | 120 | 125 mT |
| Secondary Drying | 25° C. | 375 | 950 | 125 mT |

| | | Trial 7 | | |
|---|---|---|---|---|
| Stage | Temperature | Ramp Time (min) | Hold time (min) | Vacuum |
| Freezing | −45° C. | 188 | 300 | — |
| Primary Drying | −45° C. | — | 10 | 125 mT |
| | −18° C. | 270 | 3200 | 125 mT |
| | −5° C. | 250 | 120 | 125 mT |
| Secondary Drying | 25° C. | 375 | 600 | 125 mT |

Trial 8

| Stage | Temperature | Ramp Time (min) | Hold time (min) | Vacuum |
|---|---|---|---|---|
| Freezing | −45° C. | 188 | 300 | — |
| Primary Drying | −45° C. | — | 10 | 125 mT |
|  | −18° C. | 270 | 3200 | 125 mT |
|  | −5° C. | 250 | 120 | 125 mT |
| Secondary Drying | 25° C. | 375 | 600 | 125 mT |

Trial 9

| Stage | Temperature | Ramp Time (min) | Hold time (min) | Vacuum |
|---|---|---|---|---|
| Freezing | −45° C. | 188 | 300 | — |
| Primary Drying | −45° C. | — | 10 | 125 mT |
|  | −18° C. | 270 | 3200 | 125 mT |
|  | −5° C. | 250 | 120 | 125 mT |
| Secondary Drying | 25° C. | 375 | 600 | 125 mT |

Trial 10

| Stage | Temperature | Ramp Time (min) | Hold time (min) | Vacuum |
|---|---|---|---|---|
| Freezing | −45° C. | 188 | 300 | — |
| Primary Drying | −45° C. | — | 10 | 125 mT |
|  | −18° C. | 270 | 3200 | 125 mT |
|  | −5° C. | 250 | 120 | 125 mT |
| Secondary Drying | 25° C. | 375 | 600 | 125 mT |

Trial 11

| Stage | Temperature | Ramp Time (min) | Hold time (min) | Vacuum |
|---|---|---|---|---|
| Freezing | −45° C. | 188 | 300 | — |
| Primary Drying | −45° C. | — | 10 | 125 mT |
|  | −18° C. | 270 | 3200 | 125 mT |
| Secondary Drying | −5° C. | 250 | 400 | 125 mT |

After completion of lyophilization, vials are sealed with aluminum seals.

Observation: After the lyophilization, white cake was obtained with good structure. Reconstitution of the lyophilized vial using 5.0 mL Sodium Chloride Injection resulted in clear, colorless solution. Reconstitution time was about 15 seconds.

A summary of the lyophilization trial parameters is presented in FIG. 1.

Example 2

Testing Results

Stability Testing: Finished product samples were stored in regulated ICH storage condition of 25° C./60% RH. An initial assay was run. Samples were pulled at 1, 2, 3, 6, 12 and 24 months storage and assayed. Solution pH and water content by Karl Fischer were measured at the time of sampling.

Fosaprepitant is a prodrug of Aprepitant. Fosaprepitant has higher solubility in water, i.e. about 300 mg/mL. However, Aprepitant has limited solubility in aqueous solution. Degradation of Fosaprepitant generates Aprepitant, which has limited solubility and hence it can generate sub-visible particles followed by precipitation that can be observed visually.

Particulate Matter Test: Description of reconstituted solution and particulate matter test used the USP <788> method for subvisible particles as these are the key parameters to confirm the quality of pharmaceutical solution product for injectable delivery. The risk for generating visible or sub-visible particles is higher with Fosaprepitant product containing higher Aprepitant levels.

Stability data for lyophilization trials 1-11 is shown in the tables in FIGS. 2-12.

Labels of all commercially available products describe the final reconstituted and diluted solution: "Before administration, inspect the bag for particulate matter and discoloration. Discard the bag if particulate and/or discoloration are observed." Thus, the critical quality attribute for product acceptance is particulate matter and color of final diluted solution.

Reconstituted solution stability study: To confirm the solution state stability of Fosaprepitant lyophilized product after reconstitution and final dilution at time of use, we performed reconstituted solution stability study. Reconstituted solution stability study was performed by simulating the procedure given in the label of commercially marketed product (EMEND® for Injection, 150 mg/vial). Finished product was reconstituted using 5 mL 0.9% Sodium Chloride Injection, USP. Reconstituted solution was transferred to a bag containing 145 mL of 0.9% Sodium Chloride Injection, USP to make up 150 mL solution producing final concentration of Fosaprepitant in diluted solution 1 mg/mL. Samples were collected and tested after 0 hr and 24 hrs. Results of all studies are shown in FIG. 13.

Stability study results (for 24 months at 25° C.) and reconstituted solution stability study of results (for 26 months at 25° C.), as shown in FIG. 13, indicate that there are no visible or sub-visible particles in final diluted solutions even after 24 hours with potency of the product was above 95%. Thus, the storage condition of the described Fosaprepitant lyophilized product is acceptable at room temperature. These data confirm that the product can be stored at controlled room temperature (20 to 25° C.) for at least 24 months.

As shown in FIG. 14, reconstituted solution stability study of lyophilized product with aprepitant content (about 3.7%) causes precipitation/crystallization during reconstituted solution stability study (in-use study). These results confirm that Aprepitant quantity is very critical in product. Final diluted solution with more than about 2.2% Aprepitant causes precipitation and higher sub-visible particle than the acceptance criteria given in USP <788>, while Aprepitant equal to or less than about 2.2% in final diluted product gives pharmaceutically stable Fosaprepitant lyophilized product suitable for use up to 24 hours at room temperature after dilution.

Example 3

Comparative Example

Storage Conditions: In comparison, below are the storage conditions of FDA approved and commercially available pharmaceutical products of Fosaprepitant.

| Product Name | Manufactured/Supplied by | Storage condition |
|---|---|---|
| EMEND (Fosaprepitant) for Injection, 150 mg/vial | Merck Sharp & Dohme Corp. | Emend for injection vials must be refrigerated, store at 2° C.-8° C. (36° F.-46° F.). |
| Fosaprepitant for Injection, 150 mg/vial | MSN Laboratories | Fosaprepitant for injection vials must be refrigerated, store at 2° C. to 8° C. (36° F. to 46° F.). |
| Fosaprepitant for Injection, 150 mg/vial | Fresenius Kabi USA, LLC | Fosaprepitant for injection vials must be refrigerated, store at 2° C. to 8° C. (36° F. to 46° F.). |
| Fosaprepitant for Injection, 150 mg/vial | Dr. Reddy's Laboratories Inc. | Fosaprepitant for injection vials must be refrigerated, store at 2° C.-8° C. (36° F.-46° F.). |
| Fosaprepitant for Injection, 150 mg/vial | Apotex Corp | Fosaprepitant for injection vials must be refrigerated, store at 2° C. to 8° C. (36° F. to 46° F.). |
| Fosaprepitant for Injection, 150 mg/vial | Baxter Healthcare Corporation | Fosaprepitant for Injection vials must be refrigerated, store at 2° C.-8° C. (36° F.-46° F.). |
| Fosaprepitant for Injection, 150 mg/vial | BE Pharmaceuticals Inc. | Fosaprepitant for injection vials must be refrigerated, store at 2° C. to 8° C. (36° F. to 46° F.). |
| Fosaprepitant for Injection, 150 mg/vial | SunGen Pharma, LLC | Fosaprepitant for injection vials must be refrigerated, store at 2° C.-8° C. (36° F.-46° F.). |
| Fosaprepitant for Injection, 150 mg/vial | Meitheal Pharmaceuticals Inc. | Fosprepitant for injection vials must be refrigerated, store at 2° C. to 8° C. (36° F. to 46° F.). |
| Fosaprepitant for Injection, 150 mg/vial | Actavis Pharma, Inc. | Store at 2° to 8° C. (36° to 46° F.). |

Based on this information, all current manufacturers/suppliers are supplying lyophilized Fosaprepitant product that is refrigerated and stored at 2° to 8° C. (36° to 46° F.). Products which are refrigerated and stored at 2° to 8° C. (36° to 46° F.) require special shipment (cold chain) during transportation. These products need to be kept in refrigerator in pharmacies and hospitals before use.

Aprepitant: FDA approved and marketed brand product EMEND (Fosaprepitant) for Injection, 150 mg/vial were evaluated by performing assay, pH reconstitution time, and assessing completeness and clarity of solution. Results are shown in FIG. 15.

Results, as shown in FIG. 15, indicate that Aprepitant content in the product is low likely due to the storage condition of 2° to 8° C. (36° to 46° F.). Even after expiry of the reference marketed product sample (EMEND for Injection), Aprepitant is about 0.2% w/w.

The inventor of this patent surprisingly found that the product stored at 25° C. for up to 24 months has Aprepitant from 0.5% up to 2.2% and still complies with USP requirement of Particulate Matter Test (USP <788>). This is a significant improvement in that it avoids special shipment (cold chain) during transportation and the products do not need to be kept in refrigerator in pharmacies and hospitals before use. This, in turn, avoids inadvertent degradation and potency loss when products are not transported or stored properly.

However, the inventive products are also superior in that they contain higher amounts of the therapeutically active agent, Aprepitant, but are able to control such amounts of Aprepitant to those that facilitate parenteral administration and do not pose issues upon reconstitution and dilution. Such compositions are likely to provide relief to patients more rapidly than existing product while also qualifying as generic equivalents that can be provided at lower costs. Prior to the inventive processes and composition, such an optimal solid composition was not achieved.

While the present teachings have been described above in terms of specific embodiments and examples, it is to be understood that they are not limited to those disclosed embodiments and examples. Many modifications to the embodiments and examples will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the data tables.

What is claimed is:

1. A process for preparing solid Fosaprepitant compositions that are stable after long term storage at room temperature, the process comprising the steps of:
    dissolving Fosaprepitant active ingredient and excipients in water to form a Fosaprepitant solution;
    filtering the Fosaprepitant solution;
    filling the filtered solution into a primary packaging container;
    partially stoppering the primary packaging container;
    freezing the solution in the primary packaging container at a first freezing temperature;
    applying vacuum at second temperature that is higher than the freezing temperature;
    fully stoppering the primary packaging container; and
    sealing the stoppered primary packaging container,
    wherein the solution is held for up to about 72 hours before and/or after the step of filtering and prior to the step of filling.

2. The process of claim 1, wherein the step of dissolving comprises dissolving the Fosaprepitant active ingredient and excipients in a first quantity of water and then subsequently adding a second quantity of water.

3. The process of claim 1, wherein the primary packaging container is a vial and the step of partially stoppering comprises half stoppering the vial.

4. The process of claim 1, wherein the freezing temperature is about −35° C. to about −55° C.

5. The process of claim 1, wherein the second temperature is about −25° C. to about −5° C.

6. The process of claim 1, wherein the vacuum is about 500 mT to about 100 mT.

7. The process of claim 1, wherein after the step of the applying vacuum the process further comprises the step of secondary drying at a temperature greater than 0° C.

8. The process of claim 2, wherein the excipients comprise a surface active agent.

9. The process of claim 8, wherein the concentration of surface active agent in the Fosaprepitant solution is 10 mg/mL to 30 mg/mL.

10. The process of claim 1, wherein the excipients comprise at least one of a chelating agent and a bulking agent.

11. The process of claim 1, further comprising the step of adjusting the pH of the Fosaprepitant solution to be between pH 7 and 9.5.

12. The process of claim 1, wherein the Fosaprepitant active ingredient is Fosaprepitant Dimeglumine.

13. The process of claim 1, wherein the Fosaprepitant solution has a concentration of about 5 mg/mL to about 150 mg/mL Fosaprepitant.

14. The process of claim 2, wherein the excipients comprise a bulking agent, surface active agent, and chelating agent.

15. The process of claim 2, wherein the excipients consist of Polysorbate 80, lactose, povidone, and Disodium Edetate.

16. The process of claim 8, wherein the surface active agent is Polysorbate 80.

17. A process for preparing solid Fosaprepitant compositions that are stable after long term storage at room temperature, the process comprising the steps of:
dissolving Fosaprepitant active ingredient and excipients in water to form a Fosaprepitant solution;
filtering the Fosaprepitant solution;
filling the filtered solution into a primary packaging container;
partially stoppering the primary packaging container;
freezing the solution in the primary packaging container at a first freezing temperature;
applying vacuum at second temperature that is higher than the freezing temperature;
fully stoppering the primary packaging container;
sealing the stoppered primary packaging container; and
storing the stoppered primary packaging container at about 25° C. for about 6 months, wherein the stored Fosaprepitant contains less than 2.5% Aprepitant.

18. The process of claim 17, wherein the solution is held for up to about 72 hours before and/or after the step of filtering and prior to the step of filling.

19. The process of claim 17, wherein the step of dissolving comprises dissolving the Fosaprepitant active ingredient and excipients in a first quantity of water and then subsequently adding a second quantity of water, the excipients consisting of Polysorbate 80, lactose, povidone, and Disodium Edetate.

20. The process of claim 19, further comprising the step of adjusting the pH of the Fosaprepitant solution to about 7 to about 9.5.

* * * * *